US00PP36983P2

(12) United States Plant Patent
Bourne

(10) Patent No.: US PP36,983 P2
(45) Date of Patent: Sep. 30, 2025

(54) GRAPEVINE NAMED 'SV35-206-150'

(50) Latin Name: *Vitis vinifera*
Varietal Denomination: SV35-206-150

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,549

(22) Filed: Apr. 14, 2025

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./156, 205, 207
See application file for complete search history.

(56) References Cited

U.S. PATENT DOCUMENTS

PP36,805 P3 * 7/2025 Bourne ..... A01H 6/88
Plt./205

* cited by examiner

*Primary Examiner* — Karen M Redden
(74) *Attorney, Agent, or Firm* — Eric C. Cole; Baker Manock & Jensen, PC

(57) ABSTRACT

A new and distinct variety of grapevine plant named 'SV35-206-150' particularly characterized by its sweet, crisp green berries with slight muscat flavor which ripen in early August in the McFarland, California area.

6 Drawing Sheets

Latin name of the genus and species of the plant claimed: The plant claimed relates to a new and distinct variety of *Vitis vinifera.*

Variety denomination: The plant claimed shall be known as 'SV35-206-150'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* L. and hereinafter referred to as grapevine named 'SV35-206-150'. As used herein, 'grapevine' refers to all plant parts including vines, shoots, canes, tendrils, leaves, fruit and roots of grapevine named 'SV35-206-150'. Grapevine named 'SV35-206-150' is the result of an effort to produce a mid-season, green, seedless table grape with fruit characteristics and productivity superior to currently available green, seedless cultivars. This new cultivar originated from a cross conducted in May 2014 near McFarland, California, between female parent grapevine selection 'SV29-45-20' (unpatented) and male parent grapevine selection 'SV21-66-226' (U.S. Plant Pat. No. 24,531). Resultant ovules from the cross were harvested 42 days after pollination and cultured on 'Mccown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in October of 2012 and grown in the greenhouse at 29° C. with 12 hours illumination under high pressure sodium vapor lamps. The seedling population of 322 plants was planted in the field in the spring of 2014 near Delano, Calif. The new grapevine was selected from this seedling population on Jul. 18, 2016. It was then propagated by cuttings and grafted to 'Freedom' (unpatented) rootstock in March 2017. The resultant vines were planted in a trial near McFarland, Calif. in May of 2017 and were trained to a t-trellis on 2.1 meter by 3 meter spacing. The present invention has been found to retain its distinctive characteristics through two successive asexual propagations.

Grapevine named 'SV35-206-150' differs from its female parent grapevine named 'SV29-45-20' (unpatented) in that 'SV35-206-150' has berries with small, soft seed traces less than 1 mm in length while 'SV29-45-20' has partially lignified seed traces about 3 mm in length.

Grapevine named 'SV35-206-150' differs from its male parent grapevine named 'SV21-66-226' (U.S. Plant Pat. No. 24,531) in that 'SV35-206-150' has naturally large berries averaging about 10 g each while 'SV21-66-226' produces berries which are about 4 g each.

Grapevine named 'SV35-206-150' most closely resembles commercially available cultivar 'Autumn King' (U.S. Plant Pat. No. 16,284) but differs from it in that grapevine 'SV35-206-150' produces clusters of fruit which ripen in mid-July while 'Autumn King' clusters ripen in October in the Delano, California area.

SUMMARY OF THE INVENTION

The following are the most outstanding and distinguishing characteristics of the ripe fruit of this new variety when grown under normal horticultural practices near McFarland, California:

a. Berries with green skin.
b. Very firm berry texture and sweet, neutral flavor;
c. Berries which are responsive to gibberellic acid and trunk girdling applications.
d. Abundant, medium-sized bunches which ripen in mid-August in Delano, California.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from plants about 7 years old grown near McFarland, Calif. in 2024.

DETAILED BOTANICAL DESCRIPTION

Figure 1:
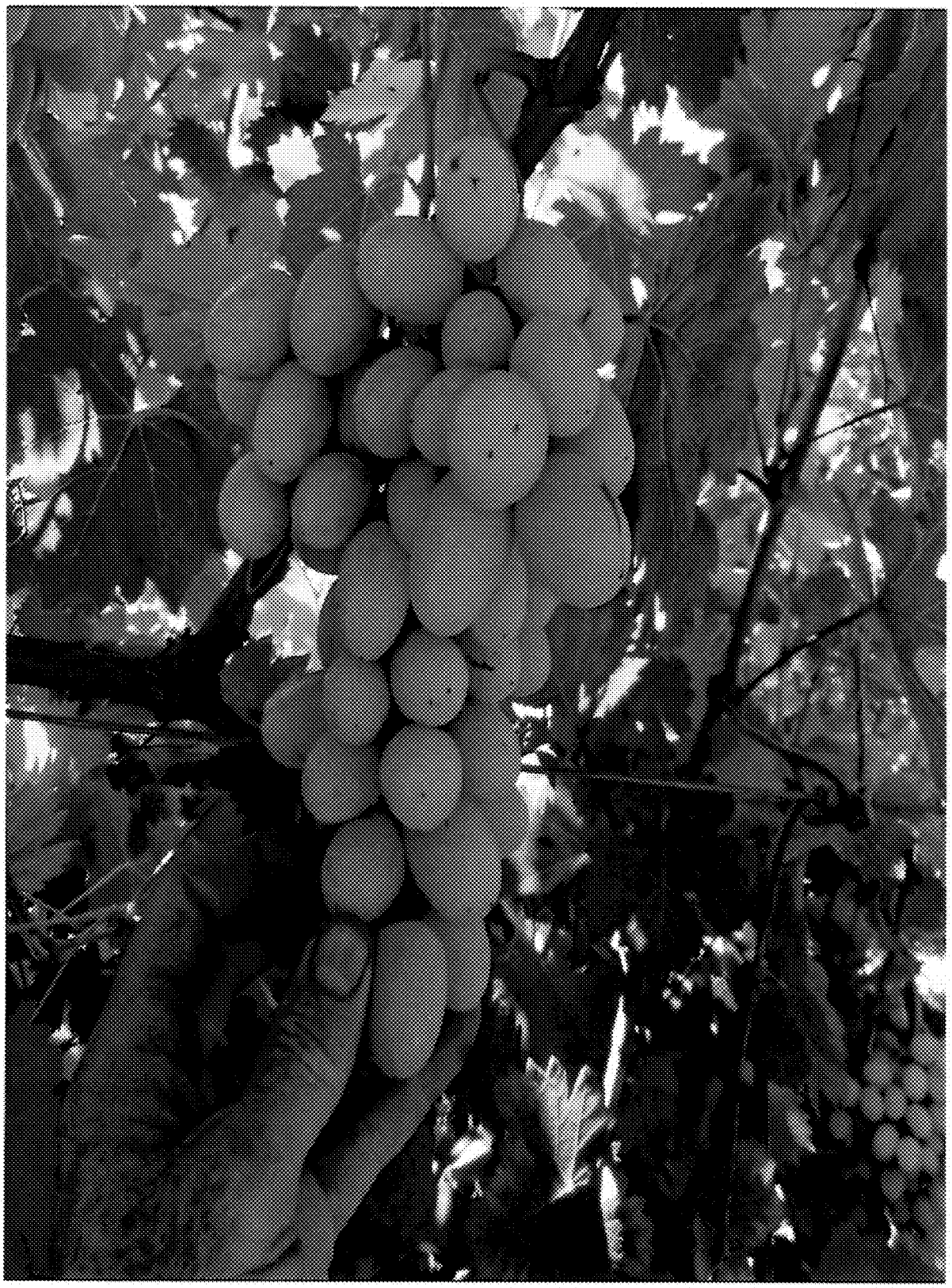
FIG. 1 Fruit clusters on seedling vine at time of selection.
Figure 2:
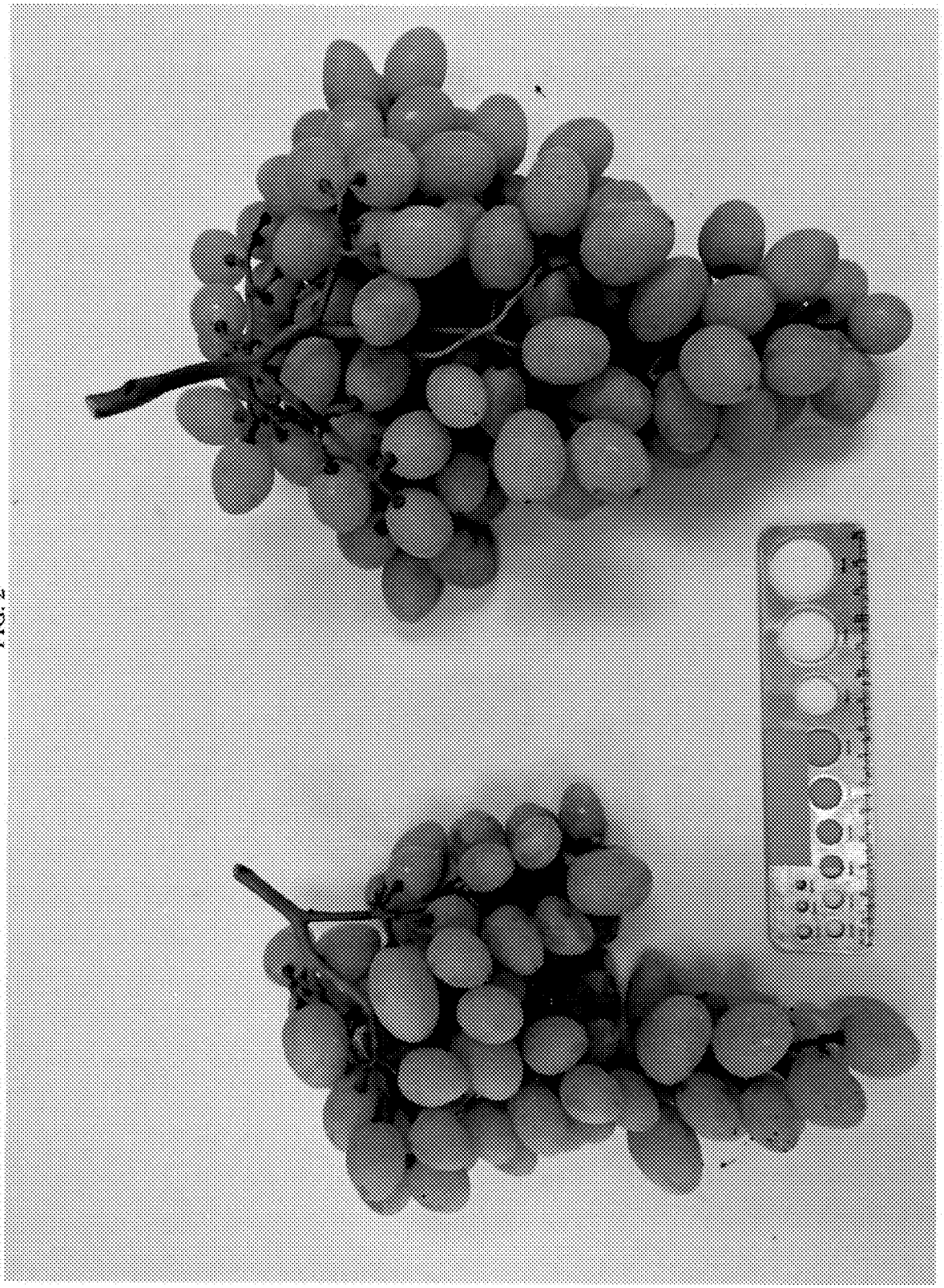
FIG. 2 Natural fruit cluster (left), fruit cluster treated with gibberellic acid and trunk girdling (right).
Figure 3:
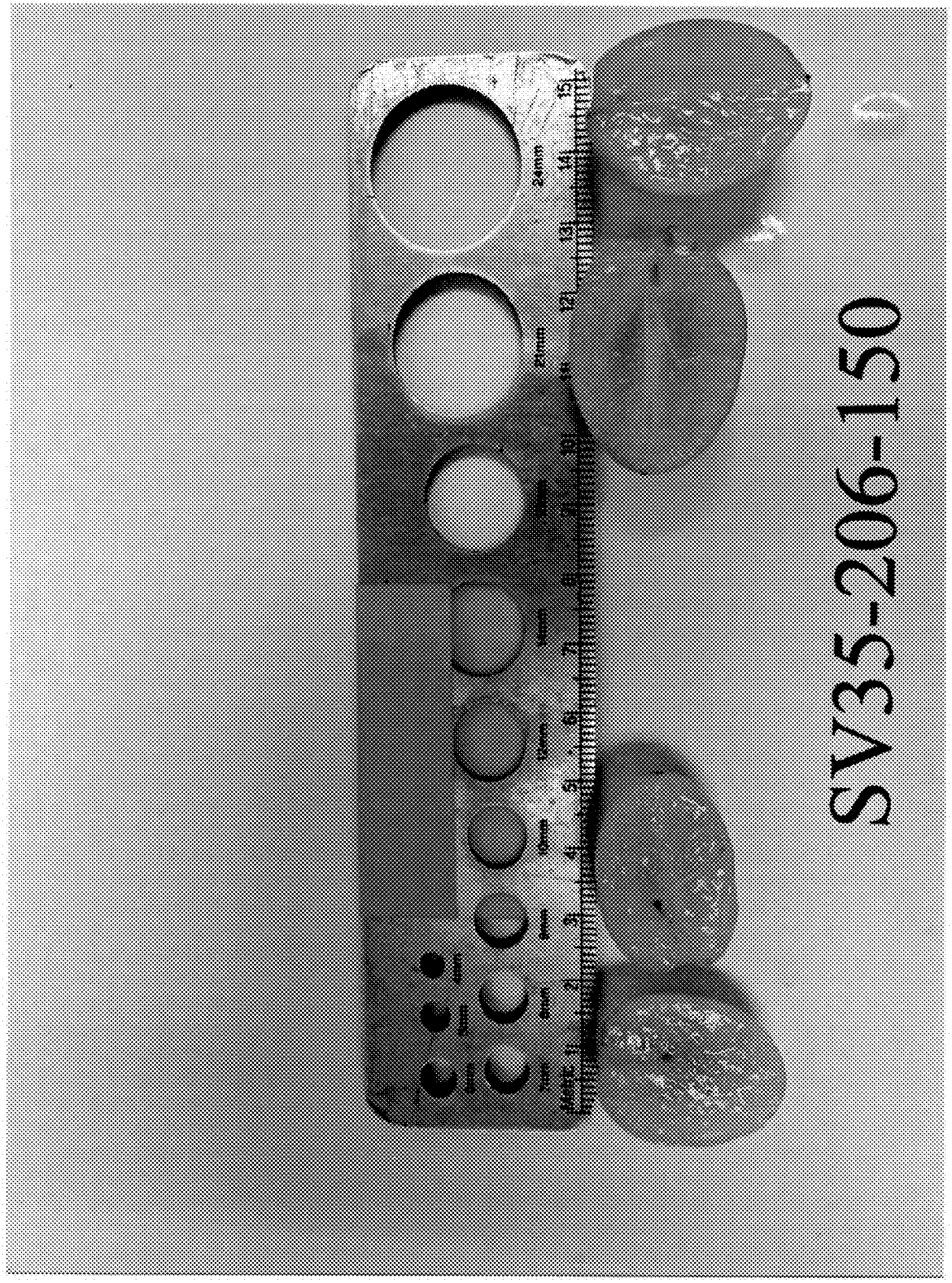
FIG. 3 Berry of natural fruit clusters (left) and berry of cluster treated with gibberellic acid and trunk girdling (right).
Figure 4:
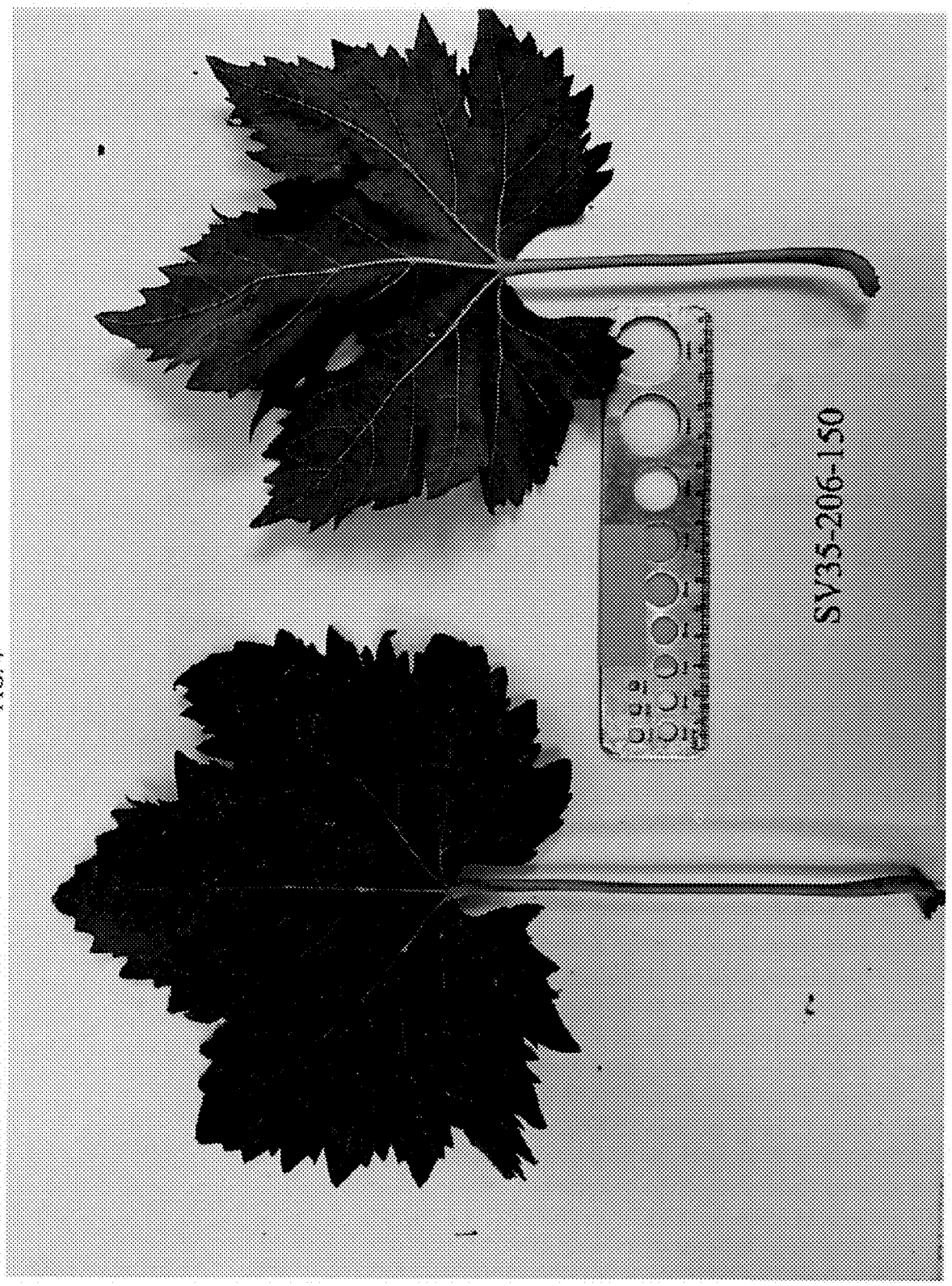
FIG. 4 Top and bottom view of leaves.
Figure 5:
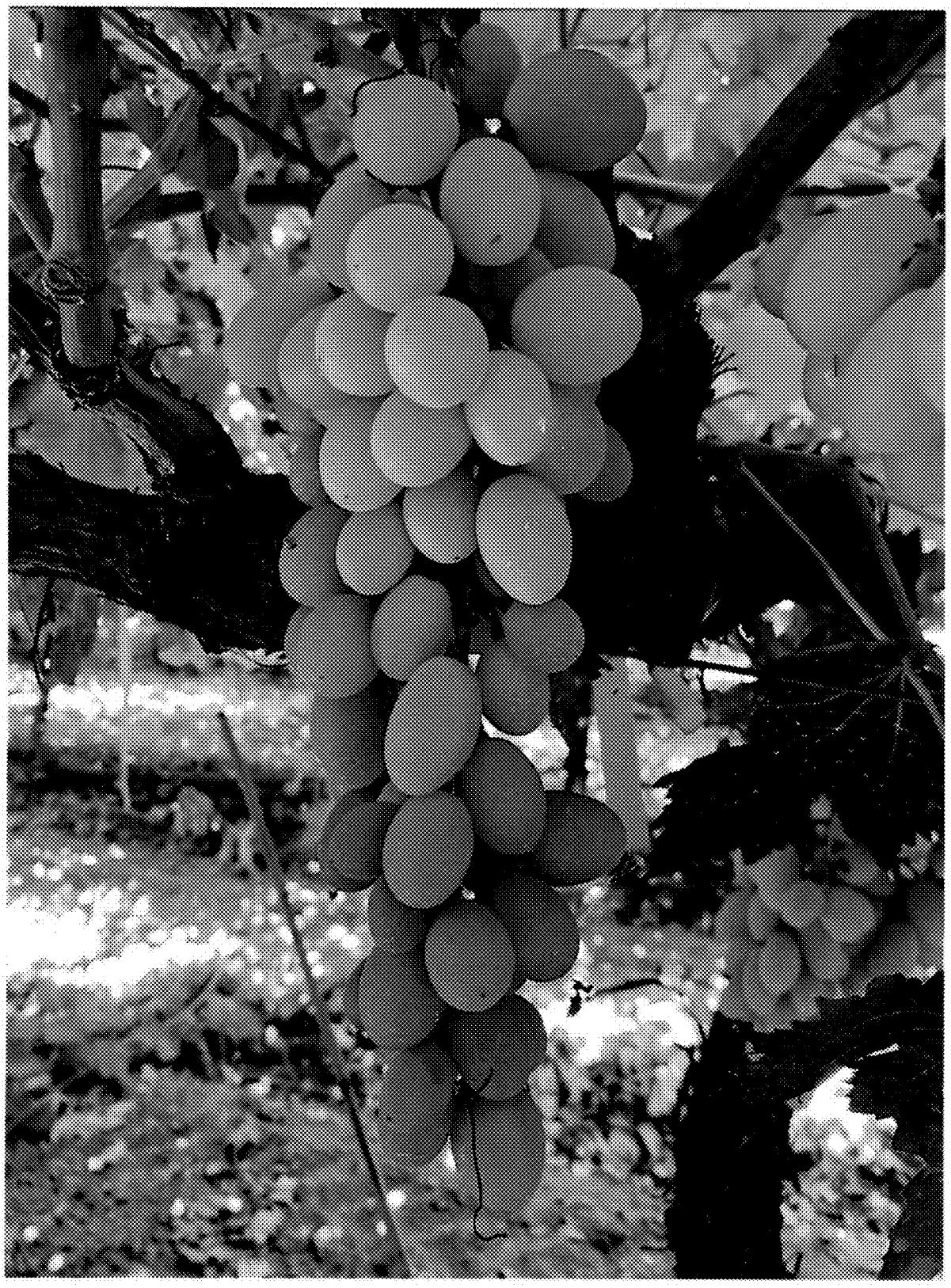
FIG. 5 Natural fruit cluster on mature vine.
Figure 6:
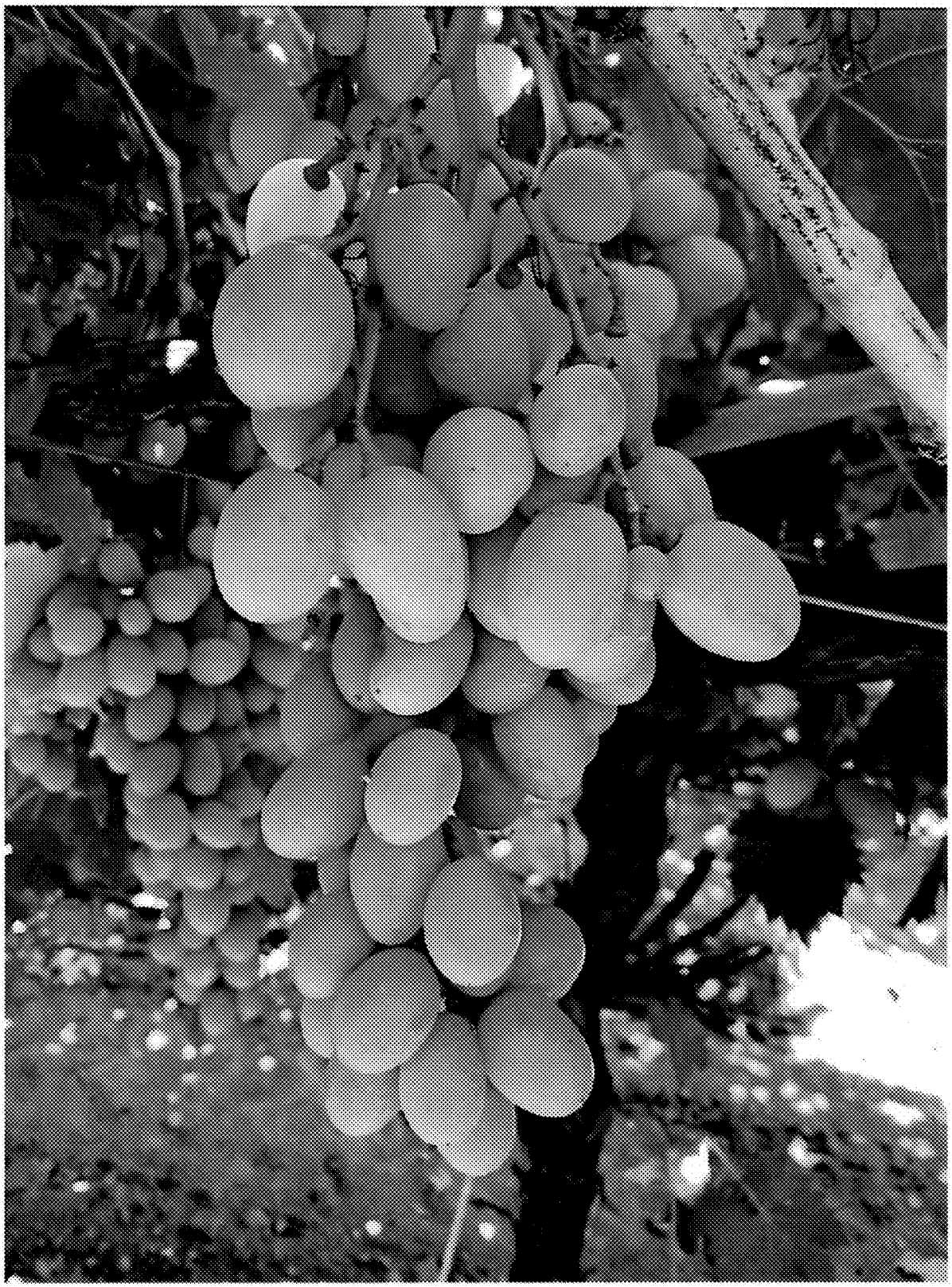
FIG. 6 Fruit cluster on mature vine treated with exogenous gibberellic acid and trunk girdling.

The following detailed description sets forth the distinctive characteristics of grapevine named 'SV35-206-150'. Descriptions of the new invention apply to vines of grapevine named 'SV35-206-150' grown on 'Freedom' (unpatented) rootstock at a density of 1,537 vines per hectare grown near McFarland, California in August of 2023. These vines were in their fifth year of production having been planted in 2017. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—'SV35-206-150'.

Plant:
- *Vigor*.—vines spur-pruned and shoot thinned to 32 shoots average 172.21 cm of growth per cane.
- *Density of foliage*.—Medium.
- *Productivity*.—Very productive, up to 41,000 kg./ha.
- *Hardiness*.—Observed to 0° C.
- *Rootstock*.—'Freedom'.

Trunk:
- *Shape*.—Broadly elliptical.
- *Straps*.—Long, split.
- *Surface texture*.—Shaggy.
- *Trunk circumference*.—27.94 cm.
- *Inner bark color*.—RHS Greyed-Orange group 179B.
- *Outer bark color*.—RHS Greyed-Green group 197A.

Mature leaves:
- *Average blade length*.—14.4 cm.
- *Average blade width*.—18.6 cm.
- *Size of blade*.—Medium.
- *Shape*.—Pentagonal.
- *Number of lobes*.—5.
- *Anthocyanin coloration of main veins on the upper side of the blade*.—Absent.
- *Mature leaf profile*.—Cupped downwards around entire margin.
- *Blistering* (*upper surface*).—Absent.
- *Leaf blade tip*.—Cupped slightly downwards.
- *Margins*.—Lobed, serrated, undulating.
- *Apex*.—Broadly acuminate.
- *Bases*.—Sagittate.
- *Thickness*.—Medium.
- *Undulation of blade between main and lateral veins*.—Slight.
- *Shape of teeth*.—Mixture of both sides straight and both sides convex.
- *Length of teeth*.—15.4 mm.
- *Width of teeth*.—15 mm.
- *Ratio length/width of teeth*.—about 1:1.
- *General shape of petiole sinus*.—Half open.
- *Tooth at petiole sinus*.—Absent.
- *Petiole sinus limited by veins*.—Absent.
- *Shape of upper lateral sinus*.—Lobes slightly-strongly overlapping.
- *Depth of upper lateral sinus*.—Shallow (avg. 1.7 cm).
- *Prostrate hairs between veins* (*lower surface*).—Absent.
- *Erect hairs between veins* (*lower surface*).—Absent.
- *Prostrate hairs on main veins* (*lower surface*).—Only erect hairs at junctions.
- *Density of erect hairs on main veins* (*lower surface*) .—Very spares, only at junctions.
- *Prostrate hairs on main veins* (*upper surface*).—Very sparse, only at central junction.
- *Upper surface*.—Summer color: RHS Yellow-Green group 147A. Surface texture: Rough. Surface appearance: Smooth. Goffering of blade: Absent.
- *Lower surface*.—Summer color: RHS Green group 137C. Anthocyanin coloration of main veins on lower leaf surface: Absent. Anthocyanin coloration on laterals: Absent. Glossiness: Low. Pubescence distal portion of surface: Absent. Surface texture: Rough. Surface appearance: Dull.
- *Petiole*.—Length: 12.0 cm. Length of petiole compared to middle vein: About equal. Density of prostrate hairs: Absent. Density of erect hairs: Absent. Shape of base of petiole sinus: Half open. Color: In shade: RHS Yellow-Green group 145A. In sun: RHS Yellow-Green group 145B.

Tendrils:
- *Number & pattern*.—Bifurcated and trifurcated; forming irregular at all nodes above node 6.
- *Length*.—21.7 cm.
- *Diameter*.—5.2 mm.
- *Texture*.—Smooth.
- *Color*.—RHS Yellow-Green group 144A.

Growing tips (young shoot):
- *Prostrate hair on tips*.—Present; sparse.

*Anthocyanin coloration of prostrate hairs on tips.*—Absent.
*Erect hairs on tip.*—Absent.
*Color.*—RHS Yellow-Green group N144C.
*Anthocyanins.*—Absent.
*Shape.*—Rounded.
*Apex.*—Fully open.

Green summer shoots:
*Shoot attitude.*—Erect.
*Internode color dorsal surface.*—RHS Yellow-Green group 144C.
*Internode color ventral surface.*—RHS Yellow-Green group 144B.
*Node color dorsal surface.*—RHS Yellow-Green group 144C.
*Node color ventral surface.*—RHS Yellow-Green group 144B.
*Density of erect hairs on internodes.*—Absent.

Woody shoot:
*Canes.*—Internode length: 10.5 cm. Width at node: 1.7 cm. Surface: Smooth.
*Buds.*—Shape: Conical. Length: 7.1 mm. Width: 5.7 mm. Height: 5.6 mm. Color: RHS Brown group 200B. Texture: Smooth.

Flowers:
*Flower sex.*—Hermaphrodite.
*Position of first flowering nodes.*—2.
*Number of inflorescences per shoot.*—1 or 2.
*Flower cluster width.*—12.6 cm.
*Flower cluster length.*—27.6 cm.
*Cluster stem color.*—RHS Yellow-Green group 145A.
*Calyptra color.*—RHS Yellow-Green group 144A.
*Ovary length.*—3 mm.
*Ovary width.*—1 mm.
*Ovary color.*—RHS Green group 143A.
*Filament length.*—2 mm.
*Filament color.*—RHS Yellow-Green group 145C.
*Anther length.*—1 mm.
*Anther color.*—RHS Yellow group 8C.
*Date of full bloom.*—May 2, 2024.

Fruit:
*Ripening period.*—Mid-season, McFarland, California.
*Date of ripening.*—Aug. 12, 2020, McFarland, California.
*Use.*—Fresh market.
*Keeping quality.*—Very good.
*Shipping quality.*—Good.
*Solids-sugar.*—High, about 20 brix at full maturity.
*Refractometer test.*—Control: 19.5 brix. Gibberellic acid and girdled: 19 brix.
*Bunch.*—Size: Large. Length (peduncle excluded): Control: 18.4 cm. Gibberellic acid and girdled: 21.2 cm. Width: Control: 14.0 cm. Gibberellic acid and girdled: 17.8 cm. Weight: Natural, without gibberellic acid treatment: 484 g. With gibberellic acid treatment: 794 g. Density: well-filled, loose. Number of berries: Control: 74. Gibberellic acid and girdled: 82. Form: Conical.
*Peduncle.*—Length (cm): Control: 5.3 cm. Gibberellic acid and girdled: 5.1 cm. Lignification (cm): None. Color: RHS Yellow-Green group 144A.
*Berry.*—Size: Large. Uniformity of size: Uniform. Weight Natural, without gibberellic acid treatment: 8.2 g. With gibberellic acid treatment: 11.6 g. Shape: Natural, without gibberellic acid treatment: Ovate. With gibberellic acid treatment: Ovate. Presence of seeds: None (other than rudimentary seeds <1 mm). Cross section: Circular. Dimensions: Longitudinal axis: Control: 2.8 cm. Gibberellic acid and girdled: 3.7 cm. Horizontal axis: Control: 2.2 cm. Gibberellic acid and girdled: 2.7 cm. Circumference: Control: 1.9 cm. Gibberellic acid and girdled: 2.5 cm. Skin color (without bloom): RHS Yellow-Green group N144D. Coloration of flesh: RHS Yellow-Green group 145C. Juiciness of flesh: Juicy. Berry firmness: Very firm. Particular flavor: Slight muscat flavor. Bloom (cuticular wax): moderate to high. Pedicel length: Control: 10.8 mm. Gibberellic acid and girdled: 11.2 mm. Berry separation from pedicel: with difficulty.
*Skin.*—Thickness: Medium. Texture: Crisp. Reticulation: Absent. Roughness: Smooth. Tenacity: Tenacious to flesh.

Ripening disease and insect resistance: No particular resistance or susceptibility has been observed. Normal disease control practices can be used.

Having thus described and illustrated our new variety of grapevine, I claim:

1. A new and distinct variety of grapevine plant named 'SV35-206-150', substantially as illustrated and described herein.

* * * * *